(12) United States Patent
Umebayashi et al.

(10) Patent No.: US 9,186,280 B2
(45) Date of Patent: Nov. 17, 2015

(54) SHEET MATERIAL SHAPING APPARATUS

(71) Applicant: ZUIKO CORPORATION, Osaka (JP)

(72) Inventors: Toyoshi Umebayashi, Osaka (JP); Takahiro Shimada, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 0 days.

(21) Appl. No.: 14/369,792

(22) PCT Filed: Nov. 7, 2012

(86) PCT No.: PCT/JP2012/078812
§ 371 (c)(1),
(2) Date: Jun. 30, 2014

(87) PCT Pub. No.: WO2013/105330
PCT Pub. Date: Jul. 18, 2013

(65) Prior Publication Data
US 2014/0356473 A1 Dec. 4, 2014

(30) Foreign Application Priority Data
Jan. 11, 2012 (JP) .................................. 2012-003161

(51) Int. Cl.
*B29C 43/46* (2006.01)
*A61F 13/15* (2006.01)
(Continued)

(52) U.S. Cl.
CPC ......... *A61F 13/15731* (2013.01); *B29C 51/225* (2013.01); *A61F 2013/15715* (2013.01); *B29C 51/082* (2013.01)

(58) Field of Classification Search
CPC ................ B29C 51/082; B29C 51/225; A61F 13/15731; A61F 13/15715
USPC ................ 425/363, 369, 471; 101/6; 162/362
See application file for complete search history.

(56) References Cited

U.S. PATENT DOCUMENTS 6,846,172 B2 * 1/2005 Vaughn et al. ................. 425/363
8,713,972 B2 * 5/2014 Lakota et al. ................... 65/185
(Continued)

FOREIGN PATENT DOCUMENTS

| CN | 1572457A | A | 2/2005 |
|----|----------|---|--------|
| JP | H09-141739 | A | 6/1997 |
| JP | 2004142182 | A | 5/2004 |
| JP | 2004-174234 | A | 6/2004 |
| JP | 2006-297786 | A | 11/2006 |

OTHER PUBLICATIONS

International Preliminary Report on Patentability in corresponding PCT/JP2012/078812 dated Jul. 15, 2014. (English Translation).
(Continued)

*Primary Examiner* — Joseph S Del Sole
*Assistant Examiner* — Thukhanh T Nguyen
(74) *Attorney, Agent, or Firm* — Marshall, Gerstein & Borun LLP (57) ABSTRACT

The invention relates to positioning of shaping rolls and makes it possible the rapid formation of a large number of fine three-dimensional shapes on a sheet material. A pair of shaping rolls that are parallel to each other include, on circumferential surfaces thereof, recessed and protruding shapes that mesh with each other at a face-to-face position. Rotating shafts of the pair of shaping rolls are cooperatively coupled with a rotational driving means through eccentric couplings. A downstream shaping roll includes, inside a roll main body, air passages that extend in a direction of a roll shaft center and air vent holes that connect the air passages to the circumferential surface. A communication member is disposed adjacent to the end of the roll main body and includes an air intake port that can communicate with the air passages in a first preset region in a circumferential direction, and an air supply port that can communicate with the air passages in a second preset region. The air intake port is communicably connected to an air intake means, and the air supply port is communicably connected to an air supply means.

9 Claims, 5 Drawing Sheets (51) Int. Cl.
 *B29C 51/22* (2006.01)
 *B29C 51/08* (2006.01)

(56) References Cited

U.S. PATENT DOCUMENTS

2004/0140047 A1 7/2004 Sato et al.
2006/0236878 A1 10/2006 Natsume et al.
2009/0092797 A1 4/2009 Sato et al.
2011/0042011 A1 2/2011 Sato et al.

OTHER PUBLICATIONS

International Search Report in corresponding PCT/JP2012/078812 dated Feb. 19, 2013.
Written Opinion in corresponding PCT/JP2012/078812 dated Feb. 19, 2013.

* cited by examiner

SHEET MATERIAL SHAPING APPARATUS

TECHNICAL FIELD

The present invention relates to a shaping apparatus for sheet materials used for surface sheets for absorbent articles and/or the like, such as disposable diapers and sanitary napkins, and more specifically, to a shaping apparatus capable of forming a large number of fine three-dimensional shapes on a sheet material rapidly and minutely.

BACKGROUND ART

Among the surface sheets for the absorbent articles are those using a composite sheet that is made by laying a sheet material on which a large number of protruding portions are formed on top of a smooth sheet material and joining the two sheet materials at positions in between the protruding portions. The composite sheet is to be worn in such a manner that the large number of protruding portions protrude toward the skin of a wearer, thereby providing a feeling of comfort to wear as well as preventing liquid leakage effectively.

Conventionally, as a shaping apparatus forming a large number of three-dimensional shapes such as the protruding portions on a sheet material, there has been one in which a pair of rolls (hereinafter referred to as shaping rolls as well) on circumferential surfaces of which recessed and protruding shapes are formed are disposed in such a manner that their recessed and protruding shapes mesh with each other (for example, refer to Patent Literature 1). In the shaping apparatus, a large number of three-dimensional shapes are formed on a sheet material passing between the pair of shaping rolls. Then the sheet material on which the three-dimensional shapes have been formed is conveyed along with the circumferential surface of the downstream shaping roll of the pair, laid on a smooth sheet as mentioned above, and then pressed by a pressing roll that is disposed on the downstream side; the predetermined portions of the sheets are joined together, and thus a composite sheet is produced.

The pair of shaping rolls need to rotate synchronously with each other so that the recessed and protruding shapes mesh with each other. To that end, it may be considered that a rotational driving means that is cooperatively coupled with the shaping rolls includes a transmission device consisting of, for example, timing pulleys and a timing belt that runs over the timing pulleys or the like in order that its output shafts to the respective shaping rolls rotate synchronously.

However, each of the pair of shaping rolls needs to be shifted in a direction perpendicular to its shaft center for adjusting the gap between the rolls, the depth of meshing, the pressing force and so forth depending on the recessed and protruding shapes, thicknesses of the sheet materials and so on. Then, in a case where output sections of the transmission device are directly coupled to the rotating shafts of the shaping rolls, the output shafts of the rotational driving means should also be shifted together with the shaping rolls being shifted, which is not easy.

Besides, even a slightly oblique deflection of the roll shaft centers of the pair of shaping rolls from their parallel disposition results in differences in the gap between the rolls, the depth of meshing, the pressing force and so forth between one end and the other end of the shaping rolls, thereby causing a problem that three-dimensional shapes formed on the sheet material become nonuniform. Therefore, the gap between the rolls, etc. must be adjusted minutely, which has been very troublesome.

In a case where the sheet material is a surface sheet, for example, the circumferential surfaces of the shaping rolls have fine recessed and protruding shapes densely formed thereon. Specifically, recessed shapes and protruding shapes of several millimeters each in diameter are formed around 1 mm apart, for example. Besides, the shaping rolls rotate at a rate of 600 to 800 rpm, for example; thus, the surface velocity of a roll main body reaches as much as 300 to 400 m/min, although it varies with the kind, thickness, etc. of the sheet material to be produced.

As a result, there is a risk that the sheet material, after passed between the pair of shaping rolls and conveyed on the circumferential surface of the downstream shaping roll to the next process is lifted off the roll surface having the recessed and protruding shapes due to a centrifugal force and thereby cannot maintain the predetermined three-dimensional shapes; and there is also a risk that, if there is a deviation of the three-dimensional shapes on the sheet material from the recessed and protruding shapes on the surface of the shaping roll, the three-dimensional shapes on the sheet material become deformed when pressed by the pressing roll disposed on the downstream side.

Further, in a case where the three-dimensional shapes that are formed on the sheet material tightly fit the recessed and protruding shapes that are formed on the downstream shaping roll, it is not easy to separate the sheet material from the surface of the downstream shaping roll at the position where the sheet material is sent out to the next process; this may place an obstacle to sending it out to the next process and thus increases the risk that the sheet material winds around the downstream shaping roll. Thus, there has been a problem that, with use of the conventional shaping apparatus, sufficiently high shaping speed of three-dimensional shapes is not easily attained.

CITATION LIST

Patent Literature

[Patent Literature 1] Japanese Patent Unexamined Publication No. 2004-174234

SUMMARY OF INVENTION

Technical Problem

In view of the above-mentioned problems, the present invention is directed to providing a sheet material shaping apparatus that allows easy positioning of shaping rolls and is capable of forming a large number of fine three-dimensional shapes on a sheet material rapidly and minutely.

Solution to Problem

To solve the above problem, the present invention is constituted as follows. The descriptions below are based on FIGS. 1 to 7 that show an exemplary embodiment of the present invention.

Aspect 1 of the present invention relates to a sheet material shaping apparatus for forming predetermined three-dimensional shapes on a sheet material (12) passing between at least a pair of shaping rolls (3, 4) disposed parallel to each other, the pair of shaping rolls (3, 4) respectively having, on circumferential surfaces thereof, recessed and protruding shapes (6) that mesh with each other at a face-to-face position, and having rotating shafts (24) wherein at least either one of rotating shafts (24) of the pair of shaping rolls (3, 4) is cooperatively coupled with a rotational driving means (10) through an eccentric coupling (25).

Aspect 2 of the present invention relates to a sheet material shaping apparatus for forming predetermined three-dimensional shapes on a sheet material (12) passing between at least a pair of shaping rolls (3, 4) disposed parallel to each other, the pair of shaping rolls (3, 4) respectively having, on circumferential surfaces thereof, recessed and protruding shapes (6) that mesh with each other at a face-to face position, wherein a downstream shaping roll (4), which is one of the pair of shaping rolls (3, 4), conveys the sheet material (12) downstream and includes, inside a roll main body (4a), air passages (28) that extend in a direction along a roll shaft center (27) and air vent holes (29) that connect the air passages (28) to the circumferential surface; and a communication member (30) is disposed adjacent to at least one end of the roll main body (4a), the communication member (30) including an air intake port (31) that can communicate with the air passages (28) in a first d preset region (A) in a circumferential direction and an air supply port (32) that can communicate with the air passages (28) in a second preset region (B) different from the first preset region (A), the air intake port (31) being communicably connected to an air intake means, the air supply port (32) being communicably connected to an air supply means.

In Aspect 1 of the present invention, the rotating shaft of the shaping roll is cooperatively coupled with the rotational driving means through the eccentric coupling. When the shaping roll is shifted, the positional difference of the shaping roll is absorbed by the eccentric joint; therefore, although the output shaft of the rotational driving means to the shaping roll is positioned at a predetermined position, the gap between the rolls can be adjusted easily.

The eccentric coupling can be any coupling as long as the coupling transmits the rotation smoothly even when the roll shaft center, which is the rotating shaft center of the shaping roll, and the shaft center of a pulley or the like cooperatively coupled with the roll are not coaxial, is not limited to one having a specific structure, and may be, for example, a universal coupling. However, a coupling that permits the shaping roll to easily undergo a parallel shift is preferable; and a Schmidt coupling, for example, is more preferable because the axial length of the coupling is short and the roll can be shifted parallel without the tilting of the roll, and thereby the gap between the rolls can be equalized from one end to the other.

That is, since the thickness and/or weight per unit area of a sheet material may vary within the margin of acceptable error, it is preferable that the position of the shaping roll is slightly shifted depending on the variations so that the pressing force can be kept constant. In the case where the eccentric coupling is a Schmidt roll, since the parallel disposition is maintained even after the shaping roll is slightly shifted, the meshing of the fine recessed and protruding shapes can be kept uniform despite the variation of the thickness of the sheet material; thereby the predetermined three-dimensional shapes can be formed uniformly.

The pair of shaping rolls are usually each supported at either end by a bearing section, and it is preferable that both bearing sections of at least either one of the pair of shaping rolls are each positioned in such a manner as to be movable forward and backward in a direction perpendicular to the roll shaft center by an air cylinder so that a slight shift of the shaping roll is permitted while a predetermined pressing force is maintained.

In Aspect 2 of the present invention, in the first preset region, since the circumferential surface of the roll is communicably connected to the air intake means through the air vent holes, the air passages and the air intake port in this order, the suction power of the air intake means prevents the sheet material conveyed along with the circumferential surface of the roll is prevented from being lifted off the circumferential surface of the roll.

Also, in the second preset region, since the circumferential surface of the roll is communicably connected to the air supply means through the air vent holes, the air passages and the air supply port in this order, the sheet material conveyed along with the circumferential surface of the roll is pushed in such a manner as to be separated from the circumferential surface of the roll by the air supplied from the air supply means.

The downstream shaping roll can be any roll as long as the first preset region serves to convey the sheet material downstream and the second preset region serves to separate the sheet material from the circumferential surface of the roll; the first preset region and the second preset region can be set without limitation. However, in a case where a pressing roll is provided on the downstream side of the shaping rolls in a direction of conveyance of the sheet material and where the pair of the shaping rolls face each other at a first face-to-face section and the downstream shaping roll and the pressing roll face each other at a second face-to-face section, it is preferable that the first preset region is provided in such a manner as to correspond to a region between the first face-to-face section and the second face-to-face section and that the second preset region is provided in such a manner as to correspond to a region on the downstream side from the second face-to-face section in the direction of conveyance of the sheet material because then the sheet material can be held tightly on the circumferential surface of the roll at the region between the two face-to-face sections, be separated from the circumferential surface of the roll immediately after passing through the second face-to-face section, and thus be surely sent out to the next process.

It is preferable that the sheet material is heated in a state where the formed three-dimensional shapes fit the recessed and protruding shapes of the circumferential surfaces of the rolls because then the three-dimensional shapes are thermally set and thereby sustained well and the sheet material can easily be joined with, for instance, a smooth sheet material to give a composite sheet. In this case, when the air passages are formed inside the downstream shaping roll, there is a risk that the efficiency of heating the circumferential surface of the roll is reduced because the air passing through the air passages takes away heat supplied by a heating means. However, preferably when the downstream shaping roll includes the heating means at a position further away from the roll shaft center than the air passages, the heating means is disposed in the neighborhood of the circumferential surface and the heat supplied by the heating means to the circumferential surface of the roll is less likely to be taken away by the air passing through the air passages; so that the circumferential surface of the roll can be heated efficiently by the heating means.

Further, also in the sheet material shaping apparatus according to Aspect 1 of the present invention, preferably when the pressing roll is provided on the downstream side of the shaping rolls in the direction of conveyance of the sheet material, it is possible to produce a composite sheet easily by supplying a smooth sheet material to between the pressing roll and the shaping roll and joining it with the sheet material on which the three-dimensional shapes have been formed by the shaping rolls.

Advantageous Effects of Invention

Constituted and functioning as described above, the present invention produces the following effects.

(1) In Aspect 1 of the present invention, a shift of the shaping roll can be absorbed by the eccentric joint, and the output shaft of the rotational driving means to the shaping roll can be positioned at a predetermined position. As a result, positioning of the shaping roll is easy, and the gap between the rolls, the depth of meshing, the pressing force and the like can be adjusted easily; thus, a large number of fine three-dimensional shapes can evenly and easily be formed on a sheet material.

(2) In Aspect 2 of the present invention, since a sheet material is prevented from being lifted from the circumferential surface of the downstream shaping roll in the first preset region, the three-dimensional shapes that have been formed on the sheet material can be held by the recessed and protruding shapes on the circumferential surface of the roll; thereby their shapes can be sustained well. Also, since the sheet material can be pushed in such a manner as to be separated from the circumferential surface of the roll by the air supplied from the air supply means in the second preset region, the three-dimensional shapes that have been formed on the sheet material can be surely taken out of the recessed and protruding shapes on the circumferential surface of the roll, and thus be easily separated from the circumferential surface of the roll. As a result, a large number of fine three-dimensional shapes can rapidly and minutely be formed on a sheet material.

DESCRIPTION OF EMBODIMENTS

The present invention is concretely described below, referring to the drawings.

Figure 1:
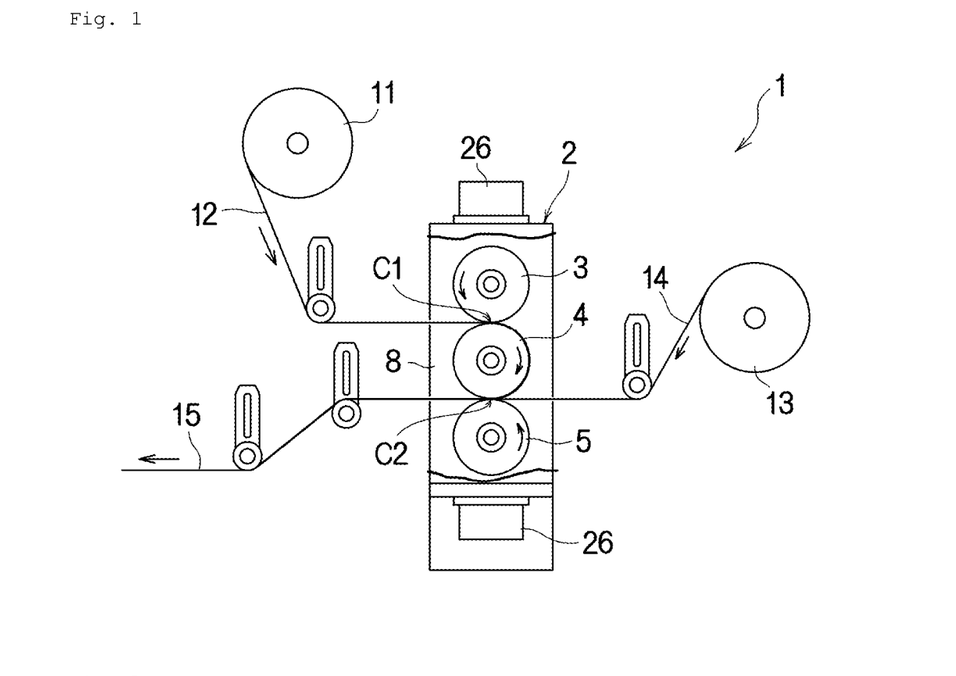
FIG. 1 is a drawing showing a general configuration of a shaping apparatus according to an embodiment of the present invention used in a composite sheet production apparatus.

FIG. 1 is a drawing showing a general configuration of a composite sheet production apparatus (1) comprising a shaping apparatus (2) according to an embodiment of the present invention; by the shaping apparatus (2), a first sheet material (12) that is supplied from a first feed section (11) and a second sheet material (14) that is supplied from a second feed section (13) are joined together to produce a composite sheet (15).

Figure 4:
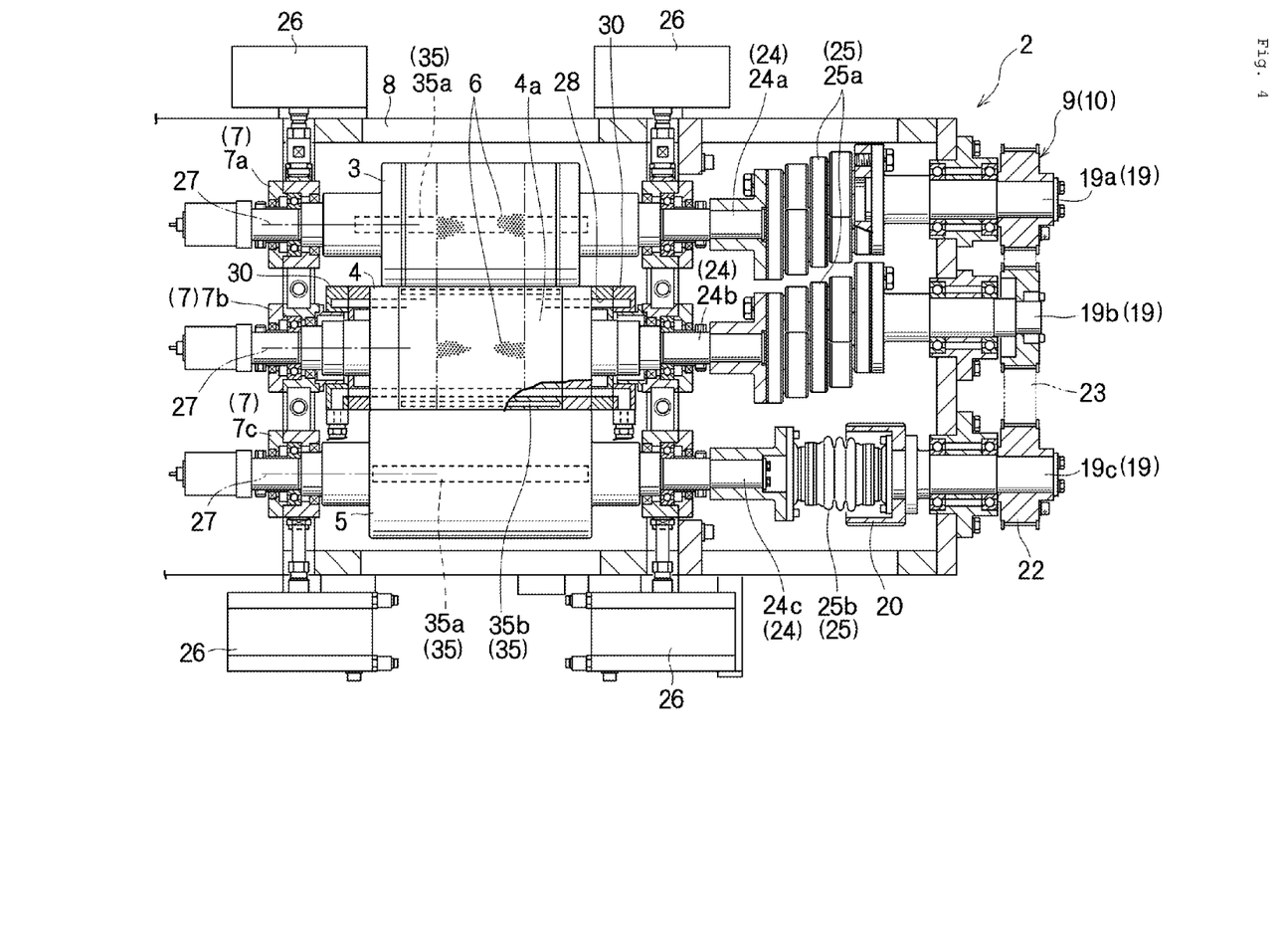
FIG. 4 is a partially cutaway front view of a shaping apparatus according to the embodiment of the present invention.

The shaping apparatus (2) includes a pair of shaping rolls (3, 4), and a pressing roll (5) disposed thereunder; the rolls (3, 4, 5) are disposed, as shown in FIG. 4, in such a manner that respective roll shaft centers (27) are parallel to each other.

The pair of shaping rolls (3, 4) face each other at a first face-to-face section (C1), and the shaping roll (4) on the lower side and the pressing roll (5) face each other at a second face-to-face section (C2). The first sheet material (12) is supplied to the first face-to-face section (C1), and is conveyed, by the shaping roll (4) on the lower side, in other words, the shaping roll (4) on the downstream side in a direction of conveyance, approximately halfway along the circumferential surface of the roll to the second face-to-face section (C2). On the other hand, the second sheet material (14) is supplied to the second face-to-face section (C2), and is compressed together with the first sheet material (12) between the downstream shaping roll (4) and the pressing roll (5); the predetermined portions of the sheets are joined together and thus a composite sheet is produced. Then the composite sheet (15) is separated from the downstream shaping roll (4) and the pressing roll (5), and is sent out of the shaping apparatus (2) to the next process.

Figure 2:
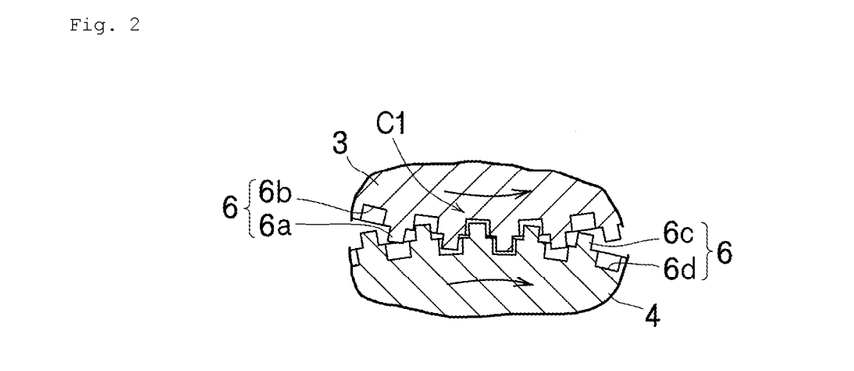
FIG. 2 is an enlarged end view of a neighborhood of a meshing section of shaping rolls according to the embodiment of the present invention.

As shown in FIG. 2, on respective circumferential surfaces of the pair of shaping rolls (3, 4) are formed recessed and protruding shapes (6) that mesh with each other at the first face-to-face section (C1). That is, at the first face-to-face section (C1), the protruding shapes (6a) formed on the circumferential surface of the shaping roll (3) on the upper side fit in the recessed shapes (6d) formed on the circumferential surface of the downstream shaping roll (4) on the lower side, and the protruding shapes (6c) formed on the circumferential surface of the downstream shaping roll (4) fit in the recessed shapes (6b) formed on the circumferential surface of the shaping roll (3) on the upper side.

Figure 3:
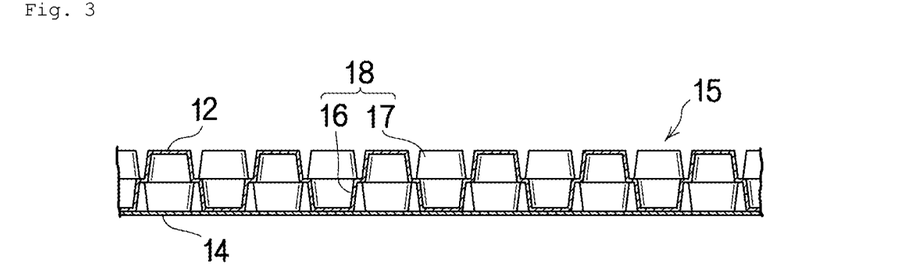
FIG. 3 is a sectional view of a composite sheet.

Passing between the pair of shaping rolls (3, 4), the first sheet material (12) is given three-dimensional shapes (18) consisting of recessed portions (16) and protruding portions (17) corresponding to the recessed and protruding shapes (6), as shown in FIG. 3. On the other hand, the second sheet material (14) is of smooth surface, and is joined with the bottom surfaces of the recessed portions (16) of the first sheet material (12) at the second face-to-face section (C2).

As shown in FIG. 4, the rotating shaft (24) of each of the rolls (3, 4, 5) is supported at either end via a bearing section (7) by a housing (8).

The bearing sections (7b) supporting the downstream shaping roll (4) located vertically in the middle are adjusted to predetermined positions and are then fixed. In contrast, the bearing sections (7a, 7c) for the upper shaping roll (3) and the pressing roll (5) are each positioned and supported in such a manner as to be movable in vertical direction, in other words, forward and backward in a direction perpendicular to the roll shaft center (27) by air cylinders (26) respectively disposed in the upper part and the lower part of the housing (8).

The shaping apparatus (2) according to the embodiment includes, as a rotational driving means (10), a transmission device (9) disposed on one side of the housing (8), and a driving source (not shown) such as a motor or the like.

Figure 5:
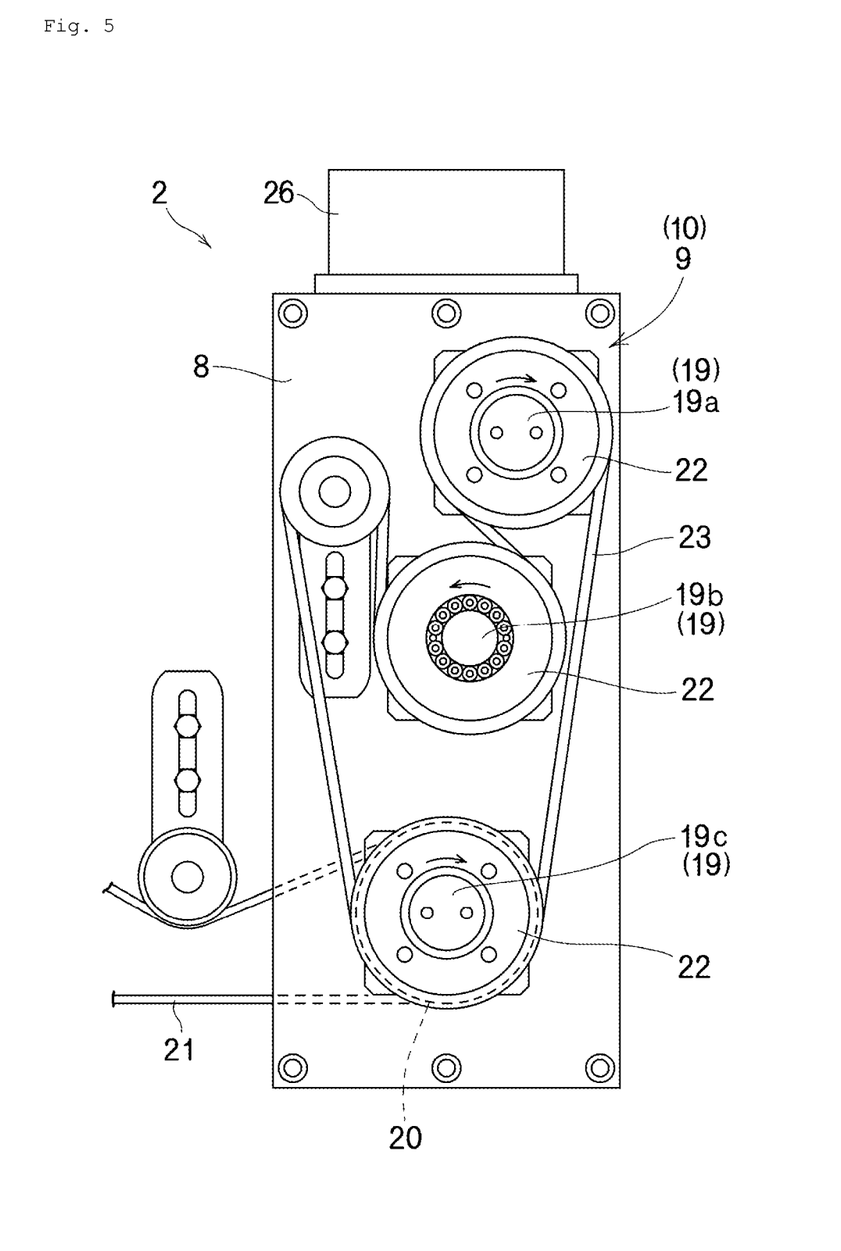
FIG. 5 is a side view of the shaping apparatus according to the embodiment of the present invention.

As shown in FIG. 4 and FIG. 5, the transmission device (9) includes output shafts (19) to the respective rolls (3, 4, 5). Among the output shafts (19), the output shaft (19c) to the pressing roll (5) has an input pulley (20) attached thereto, and the input pulley (20) is cooperatively coupled with the driving source (not shown) via a timing belt (21). Meanwhile, an end of each of the output shafts (19) has a timing pulley (22) attached thereto. Over the timing pulleys (22), a second timing belt (23) runs; thereby the respective output shafts (19) are cooperatively coupled with each other so as to synchronously rotate.

As shown in FIG. 5, the timing pulleys (22) are disposed at predetermined positions of the transmission device (9), and are not vertically aligned with each other. Therefore, the centers of the rotating shafts (24) of the respective rolls (3, 4, 5) vertically aligned with each other do not coincide with the centers of the output shafts (19) of the transmission device (9). For the reason, the rotating shafts (24) of the respective rolls (3, 4, 5) are cooperatively coupled with the respective output shafts (19) of the transmission device (9) through eccentric couplings (25), respectively. More specifically, as shown in FIG. 4, the rotating shafts (24a, 24b) of the pair of shaping rolls (3, 4) are cooperatively coupled with the output shafts (19a, 19b) through Schmidt couplings (25a), respectively whereas the rotating shaft (24c) of the pressing roll (5) is cooperatively coupled with the output shaft (19c) through a universal coupling (25b). Therefore, the pair of shaping rolls (3, 4) and the pressing roll (5) can be disposed at any adjusted positions while the output shafts (19) of the transmission device (9) are fixedly disposed at predetermined positions.

The Schmidt coupling (25a) includes three pieces of discs and links connecting between the discs. The outside discs can change their relative position through the change of disposition of the links, and while the output shaft (19) and the rotating shaft (24) fixed to the outside discs, respectively, are kept parallel to each other, the rotation of the output shaft (19) can smoothly be transmitted to the rotating shaft (24).

Depending on the changes in the thickness of the first sheet material (12), the upper shaping roll (3) is slightly shifted in vertical direction, resisting the pressing force of the air cylinder (26); however, since the rotating shaft (24a) of the upper shaping roll (3) and the output shaft (19a) of the transmission device (9) are cooperatively coupled with each other through the Schmidt coupling (25a), the upper shaping roll (3) is kept horizontal and shifted parallel without any postural inclination. As a result, the gap between the pair of shaping rolls (3, 4) is kept constant from one end to the other; thus, uniform three-dimensional shapes (18) are formed through meshing of the recessed and protruding shapes (6).

Figure 6:
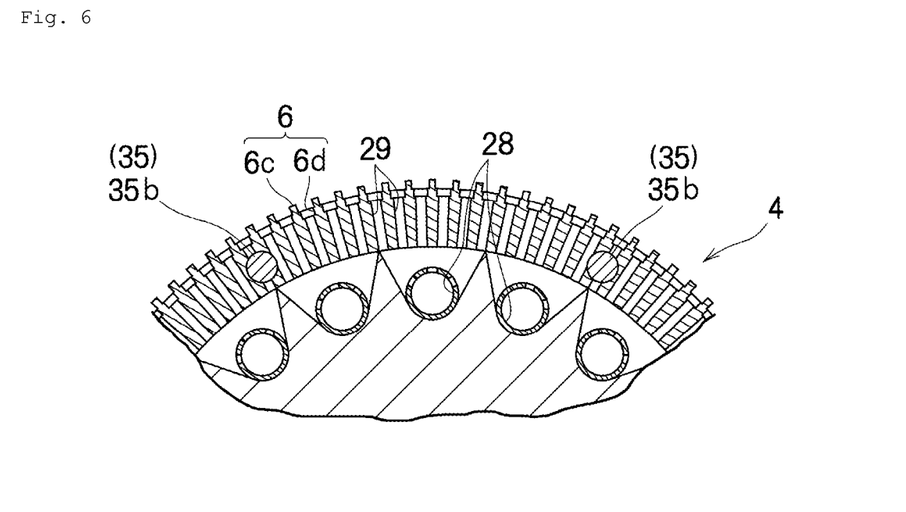
FIG. 6 is a sectional view of an essential part of a downstream shaping roll according to the embodiment of the present invention.

As shown in FIG. 4, the downstream shaping roll (4) includes, inside a roll main body (4a), a plurality of air passages (28) extending in a direction parallel to the roll shaft center (27). The air passages (28) are disposed along the circumferential surface of the roll as shown in FIG. 6, and are respectively connected to the recessed shapes of the recessed and protruding shapes (6) formed on the circumferential surface of the roll through air vent holes (29).

In the neighborhood of either end of the roll main body (4a) is disposed a communication member (30), and the communication member (30) is non-rotatably fixed to the housing (8).

Figure 7:
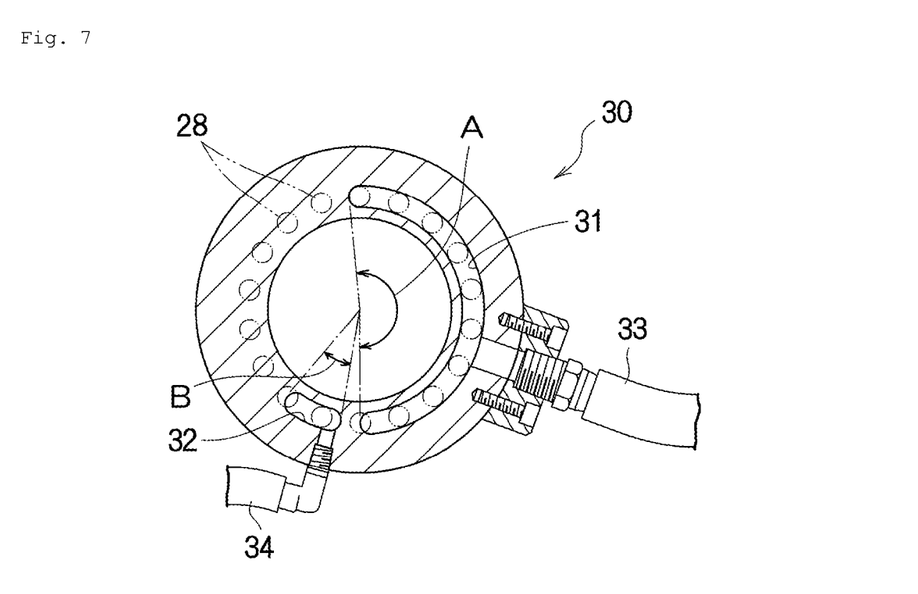
FIG. 7 is a sectional view of a communication member according to the embodiment of the present invention.

As shown in FIG. 7, the communication member (30) includes an air intake port (31) that can communicate with the air passages (28) in a first preset region (A) corresponding to a region between the first face-to-face section (C1) and the second face-to-face section (C2) in the circumferential direction, and an air supply port (32) that can communicate with the air passages (28) in a second preset region (B) corresponding to a region on the downstream side from the second face-to-face section (C2) in the direction of conveyance of the sheet material. The air intake port (31) is communicably connected to an air intake means (not shown) through an air intake path (33), and the air supply port (32) is communicably connected to an air supply means (not shown) through an air supply path (34).

The first sheet material (12) having passed between the pair of shaping rolls (3, 4) at the first face-to-face section (C1) is conveyed along with the circumferential surface of the downstream shaping roll (4) to the second face-to-face section (C2). At this time, the circumferential surface of the roll is communicably connected to the air intake means through the air vent holes (29), the air passages (28), the air intake port (31) formed in the first preset region (A), and the air intake path (33) in this order. As a result, the first sheet material (12) is sucked onto the circumferential surface of the roll by the suction power of the air intake means, and thereby is prevented from being lifted off the circumferential surface of the roll.

The first sheet material (12) having reached the second face-to-face section (C2) is, together with the second sheet material (14), compressed between the downstream shaping roll (4) and the pressing roll (5) as described above, and thereby a composite sheet (15) is produced. On the downstream side of the second face-to-face section (C2), the circumferential surface of the downstream shaping roll (4) is communicably connected to the air supply means through the air vent holes (29), the air passages (28), the air supply port (32) formed in the second preset region (B), and the air supply path (34) in this order. As a result, the composite sheets (15) having passed the second face-to-face section (C2) is pushed in such a manner as to be separated from the circumferential surface of the roll by air supplied from the air supply means, and thereby is smoothly separated from the downstream shaping roll (4) and sent out to the next process.

As shown in FIG. 4, the rolls (3, 4, 5) each include a heating means (35). That is, in the center part of the upper shaping roll (3) and the pressing roll (5), a heating means (35a) is disposed along the roll shaft center (27). The thus disposed heating means uniformly heats the circumferential surfaces of the upper shaping roll (3) and the pressing roll (5) to a predetermined temperature.

In contrast, the downstream shaping roll (4), as shown in FIG. 4 and FIG. 6, includes a plurality of heating means (35b) that are disposed at positions further away from the roll shaft center (27) than the air passages (28), or in other words, closer to the circumferential surface of the roll than the air passages (28).

Since the heating means (35b) of the downstream shaping roll (4) are disposed in the neighborhood of the circumferential surface of the roll, the circumferential surface of the roll is heated efficiently. Moreover, since the air passages (28) are disposed not between the heating means (35b) and the circumferential surface of the roll but across the heating means (35b) from the circumferential surface of the roll, the heat supplied by the heating means (35) to the circumferential surface of the roll is less likely to be taken away by the air passing through the air passages; so that the circumferential surface of the roll is heated efficiently also in this respect.

As a result, the first sheet material (12) that is supplied to between the pair of shaping rolls (3, 4) and then conveyed by the downstream shaping roll (4) is efficiently heated by the heating means (35b) and thereby is shaped well, and the second sheet material (14) that is supplied to between the downstream shaping roll (4) and the pressing roll (5) is heated by the heating means (35a) and thereby is joined well with the first sheet material (12). The second sheet material (14) may be directly supplied to the second face-to-face section (C2) as shown in FIG. 1 or alternatively be supplied to the circumferential surface of the pressing roll (5) and then be guided by the circumferential surface of the roll to the second face-to-face section (C2); in this case the second sheet material (14) can be preheated by the heating means (35a).

The sheet material shaping apparatus described above is only an exemplary embodiment of the technical idea of the present invention. The shape, structure, arrangement, dimension and the like of the members are not limited to those described in the embodiment, and various changes can be made within the scope of claims of the present invention.

For example, in the embodiment, the transmission device included in the rotational driving means consists of the timing pulleys and the timing belt that runs over the timing pulleys, and the configuration is preferable because the output shafts to which the timing pulleys are attached can be disposed freely. However, the transmission device of the present invention can be any transmission device that does not require shifting the output shafts to the shaping rolls; for example, it may be one in which a combination of gears or the like is used.

Also, in the embodiment, in the pair of shaping rolls, recessed and protruding shapes consisting of recessed shapes and protruding shapes are formed on the respective circumferential surfaces of the rolls. However, in the present invention, a configuration such that only protruding shapes are formed on a circumferential surface of one shaping roll while only recessed shapes are formed on a circumferential surface of the other shaping roll may also be acceptable.

Further, in the embodiment, the rotating shafts of the pair of shaping rolls are each cooperatively coupled with the rotational driving means through the Schmidt coupling. However, in the present invention, it is only necessary that at least either one of the rotating shafts of the shaping rolls should be cooperatively coupled with a rotational driving means through an eccentric coupling; thus, the eccentric coupling may be of other types such as universal coupling or the like. Moreover, the other shaping roll can be directly connected to the output shaft of the rotational driving means.

Also, in the embodiment, air cylinders are used for positioning of the bearing sections of one of the shaping rolls and the pressing roll in such a manner that the bearing sections are movable forward and backward in a direction perpendicular to the roll shaft center. However, in the present invention, the bearing sections may each be supported by another means such as, for example, a spring force or the like.

In the embodiment, the shaping rolls and the pressing roll are vertically aligned with each other. However, in the present invention, these rolls may be arranged in a different way, for example, at positions forming an L-shape when viewed from a side; therefore, the relative position of the second face-to-face section to the first face-to-face section is not limited to the one described in the embodiment.

Also, in the embodiment, the pair of shaping rolls and the pressing roll are virtually of the same diameter and therefore can desirably be synchronized without difficulty so that circumferential velocities of the respective rolls agree with each other. However, in the present invention, the rolls may be of different diameters. For example, the downstream shaping roll may have a larger diameter so that the sheet material conveyed by the downstream shaping roll is sufficiently heated by the downstream shaping roll and thereby surely given predetermined three-dimensional shapes and surely joined with the second sheet material. Meanwhile, the upstream shaping roll and the pressing roll may each be of a smaller diameter to reduce installation space, equipment cost, etc.

In the embodiment described above, only a single pressing roll is provided. However, in the present invention, a plurality of pressing rolls may be provided in such a manner as to respectively face the downstream shaping roll sequentially; in this case, desirably, the first sheet material and the second sheet material can be joined together more securely.

Dimensions such as diameters and lengths of the shaping rolls and the press roll, numbers of the air passages and the heating means provided, shapes, sizes and spacing of the recessed and protruding shapes, etc., needless to say, are not limited to those described in the embodiment.

INDUSTRIAL APPLICABILITY

The shaping apparatus of the present invention is capable of forming a large number of fine three-dimensional shapes on a sheet material rapidly and minutely, and therefore can be suitably used specifically as an apparatus for manufacturing surface sheets of absorbent articles such as disposable diapers, sanitary napkins and/or the like, but the apparatus is also useful as apparatus for manufacturing other sheet materials having three-dimensional shapes.

REFERENCE SIGNS LIST

2 . . . sheet material shaping apparatus
3 . . . shaping roll (upper shaping roll)
4 . . . shaping roll (downstream shaping roll)
4a . . . roll main body
5 . . . pressing roll
6 . . . recessed and protruding shapes
7 . . . bearing section
7a . . . bearing section for upper shaping roll (3)
10 . . . rotational driving means
12 . . . sheet material (first sheet material)
24 . . . rotating shaft of the roll
25 . . . eccentric coupling
25a . . . Schmidt coupling
26 . . . air cylinder
27 . . . roll shaft center
28 . . . air passage
29 . . . air vent hole
30 . . . communication member
31 . . . air intake port
32 . . . air supply port
35b . . . heating means

The invention claimed is:

1. A sheet material shaping apparatus for forming predetermined three-dimensional shapes on a sheet material passing between at least a pair of shaping rolls disposed parallel to each other, the pair of shaping rolls respectively having, on circumferential surfaces thereof, recessed and protruding shapes that mesh with each other at a face-to-face position, wherein
at least either one of rotating shafts of the pair of shaping rolls is cooperatively coupled with a rotational driving means through an eccentric coupling.

2. The sheet material shaping apparatus as claimed in claim 1, wherein the eccentric coupling is a Schmidt coupling.

3. The sheet material shaping apparatus as claimed in claim 1, wherein
the pair of shaping rolls are each supported at either end by a bearing section; and
both bearing sections of at least either one of the pair of shaping rolls are each positioned in such a manner as to be movable forward and backward in a direction perpendicular to a roll shaft center by an air cylinder.

4. A sheet material shaping apparatus for forming predetermined three-dimensional shapes on a sheet material passing between at least a pair of shaping rolls disposed parallel to each other, the pair of shaping rolls respectively having, on circumferential surfaces thereof, recessed and protruding shapes that mesh with each other at a face-to-face position,
a downstream shaping roll, which is one of the pair of shaping rolls, conveys the sheet material downstream and includes, inside a roll main body, air passages that extend in a direction along a roll shaft center and air vent holes that connect the air passages to the circumferential surface; and a communication member is disposed adjacent to at least one end of the roll main body, the communication member including an air intake port that can communicate with the air passages in a first preset region in a circumferential direction and an air supply port that can communicate with the air passages in a second preset region different from the first preset region, the air intake port being communicably connected to an air intake means, the air supply port being communicably connected to an air supply means.

5. The sheet material shaping apparatus as claimed in claim 4, wherein
a pressing roll is provided on the downstream side of the pair of shaping rolls in a direction of conveyance of the sheet material;
the pair of shaping rolls face each other at a first face-to-face section while the downstream shaping roll and the pressing roll face each other at a second face-to-face section;
the first preset region is provided in such a manner as to correspond to a region between the first face-to-face section and the second face-to-face section; and
the second preset region is provided in such a manner as to correspond to a region on the downstream side from the second face-to-face section in the direction of conveyance of the sheet material.

6. The sheet material shaping apparatus as claimed in claim 4, wherein the downstream shaping roll includes a heating means at a position further away from the roll shaft center than the air passages.

7. The sheet material shaping apparatus as claimed in claim 1, wherein a pressing roll is provided on a downstream side of the pair of shaping rolls in a direction of conveyance of the sheet material.

8. The sheet material shaping apparatus as claimed in claim 4, wherein the air vent holes in the downstream shaping roll connect the air passages to the outer circumferential surface.

9. The sheet material shaping apparatus as claimed in claim 4, wherein the air intake port of the communication member communicates with a part of the air passages in the first preset region, and the air supply port communicates with another part of the air passages in the second preset region.

* * * * *